United States Patent
Shambayati

[19]

[11] Patent Number: 5,511,416
[45] Date of Patent: Apr. 30, 1996

[54] WIDE RANGE LAMINAR FLOW ELEMENT

[75] Inventor: Ali Shambayati, Tucson, Ariz.

[73] Assignee: Alicat Scientific, Inc., Tucson, Ariz.

[21] Appl. No.: 121,350

[22] Filed: Sep. 15, 1993

[51] Int. Cl.⁶ .................. F15D 1/00; G01F 5/00
[52] U.S. Cl. .................. 73/204.21; 73/861.52; 138/43
[58] Field of Search .................. 73/202, 202.5, 73/204.21, 204.22, 861.52; 138/40, 42, 43, 44

[56] References Cited

U.S. PATENT DOCUMENTS

| | | | |
|---|---|---|---|
| 1,924,125 | 8/1933 | Linderman, Jr. | 73/167 |
| 1,946,275 | 2/1934 | Collins | 73/37 |
| 2,297,408 | 9/1942 | Hardebeck | 73/202 |
| 2,591,195 | 4/1952 | Picciano | 73/204 |
| 3,220,256 | 11/1965 | Welchbrod | 73/861.52 |
| 3,805,610 | 4/1974 | Jacobs | 73/202 |
| 3,838,598 | 10/1974 | Tompkins | 73/205 |
| 3,851,526 | 12/1974 | Drexel | 73/202 |
| 3,952,577 | 4/1976 | Hayes et al. | 73/861.52 X |
| 4,118,973 | 10/1978 | Tucker et al. | 73/55 |
| 4,366,719 | 1/1983 | Bohm et al. | 73/861.76 |
| 4,418,568 | 12/1983 | Surman | 73/202 |
| 4,427,030 | 1/1984 | Jouwsma | 138/42 |
| 4,450,718 | 5/1984 | Hartemink | 138/42 X |
| 4,461,173 | 7/1984 | Olin | 73/203 |
| 4,497,202 | 2/1985 | Mermelstein | 72/202 |
| 4,524,616 | 6/1985 | Drexel et al. | 73/203 |
| 4,542,650 | 9/1985 | Renkin et al. | 73/204.26 X |
| 4,800,754 | 1/1989 | Korpi | 73/202 |

*Primary Examiner*—Richard Chilcot
*Assistant Examiner*—George M. Dombroske
*Attorney, Agent, or Firm*—Baker & Botts

[57] ABSTRACT

A wide range laminar flow element for use in differential pressure and thermal mass flowmeters is disclosed. The flow element comprises multiple rectangular channels in a single rectangular plate. The flow element contains tabs which can be selectively removed to alter the effective diameter of the flow channel. Alternatively, the laminar flow elements can be stacked to provide a larger effective diameter of the flow channel.

8 Claims, 3 Drawing Sheets

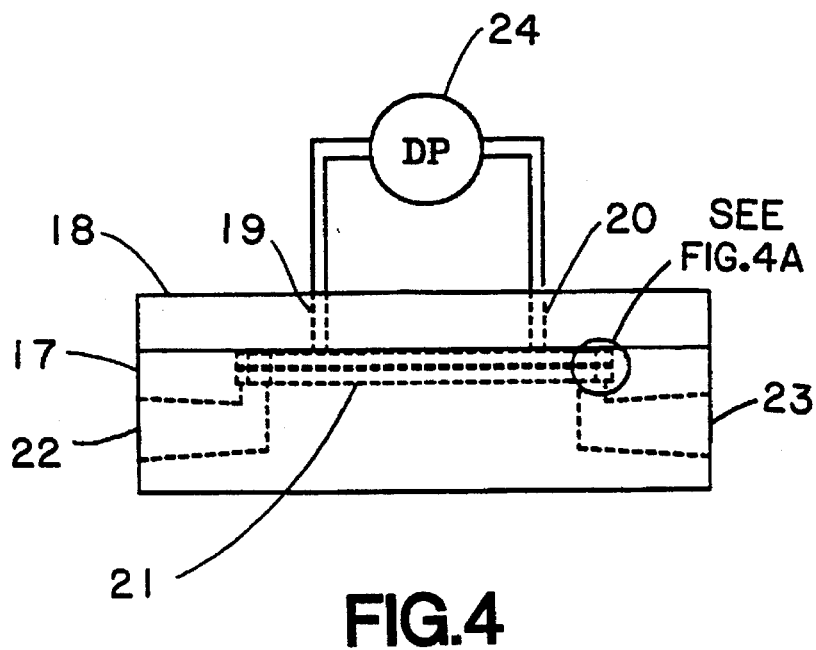
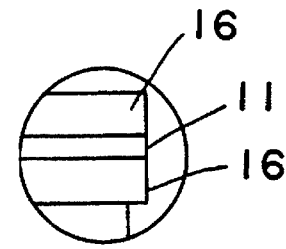
FIG.4
FIG.4A
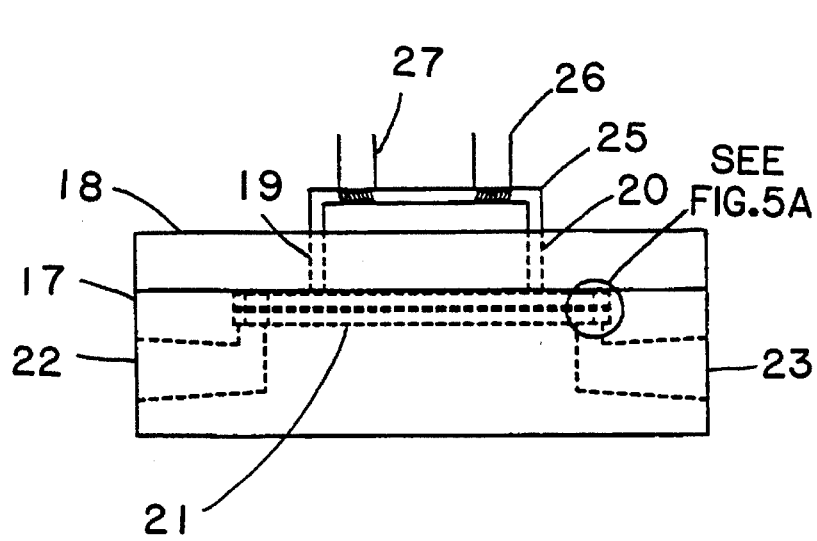
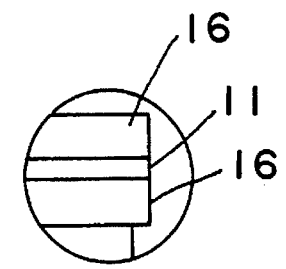
FIG.5
FIG.5A

WIDE RANGE LAMINAR FLOW ELEMENT

FIELD OF INVENTION

The present invention relates to wide range fluid flow measuring devices and more particularly to an adjustable laminar flowmeter which maintains low Reynolds numbers for a wide range of flows.

BACKGROUND OF THE INVENTION

In general, laminar flowmeters which use the linear relationship between a fluid flow rate and characteristics of the fluid, such as the change in pressure or rate of heat transfer, are known. The details of their operation are well known to those of ordinary skill in the art. Examples of flow meters are described in U.S. Pat. Nos. 4,118,973 issued to Tucker et al.; No. 4,800,745 issued to Korpi; and No. 4,427,030 issued to Jouwsma. As is also known, to produce and maintain laminar flow through such a measuring device, certain criteria have to be met. Extensive studies have been conducted to characterize these properties and the most widely used characterization is referred to as the Reynolds number. It has been determined that for smooth pipes the transition from a laminar to turbulent boundary layer occurs when the ratio of $\rho D v/\eta$ becomes larger than approximately 2,000, where $v$ is the average velocity of the fluid, $D$ is the characteristic linear dimension of the pipe, $\rho$ is the density of the fluid, and $\eta$ is the viscosity of the fluid. Preferably, to ensure laminar flow, the Reynolds number should be less than 1000.

Due to difficulties in manufacturing round pipes as laminar flow elements, attempts have been made to make laminar flow elements designed around rectangular channels. When dealing with rectangular channels, the parameters used to calculate the Reynolds number remain the same, except that $D$ is defined as the equivalent diameter by convention. Equivalent diameter, in turn, is defined as four times the hydraulic radius which is the cross-sectional area divided by the wetted perimeter. Also, the pressure drop across rectangular laminar flow elements can be calculated as $32 \eta v L/D^2$, where $\eta$ is the viscosity of the fluid, $v$ is the average velocity; $L$ is the length of the channel and $D$ is the equivalent diameter.

A difficulty in maintaining laminar flow arises when one tries to create substantial pressure drop in the flow channel. Substantial pressure drop is desired so that conventional electronics can be used to measure that pressure drop with acceptable accuracy. One way to maintain laminar flow and create substantial pressure drops at given flow rates is to make the depth of the rectangular channel substantially smaller than its length.

To enhance the usefulness of a flowmeter, it should be capable of accurately measuring the flow rate for different quantities of flow. For example, an air flowmeter that can accurately measure flow rate of 200 cc per minute, and can easily be modified to measure 1 liter per minute with the same accuracy is more in demand than a single-purpose flowmeter that is only designed for 200 cc/min. This leads to the definition of the full-scale flow rate for each flowmeter, that is, the flow rate at which the flowmeter can provide its best performance. This means that a flowmeter designed for measurement of 200 cc/min full-scale is not appropriate for use at 1 LPM, for the reason that at higher flow rate laminar flow is not ensured due to the increased mean velocity and concomitantly increased Reynolds number. A 200 cc/min flowmeter is also not appropriate for accurate measurement at substantially lower flow rates, e.g., 50 cc/min, as this requires more amplification of the signal, and hence inevitable amplification of noise.

For the reasons presented here, it is desirable to operate the flowmeter at its specified full scale flow rate. It is therefore advantageous to provide a mechanism that allows for the change in the full-scale flow rate of a flowmeter and hence optimizing the performance for different rates of flow.

To adjust the full scale flow rate, Tucker proposes a mechanism in which a number of plates with rectangular grooves are stacked on top of each other. Jouwsma proposes a method in which grooves are formed in metal disks and the metal disks are placed onto each other. Korpi proposes a conical shaped laminar flow element which is molded out of plastic and has multiple parallel channels. These channels are blocked by webbing which can be removed to change the cross section of the primary passage. While these methods provide for adjustment in the full scale range of flow, each has drawbacks and disadvantages.

SUMMARY OF THE INVENTION

The present invention provides multiple rectangular channels in a single rectangular plate. As manufactured, at least one of the channels is open to the passage of fluid, while others are blocked by tabs that can be removed to alter the diameter or effective diameter of the laminar flow channel. This design easily allows for a change in the full scale flow rate within a single flow element. Additionally, multiple such elements may be used to provide further adjustability. Alternatively, all may be blocked initially. Advantageously, the invention may be formed by chemically etching standardly available stainless steel shim stock which is readily available with high tolerances.

BRIEF DESCRIPTION OF THE DRAWINGS

FIG. 4 shows an example of a differential pressure type flowmeter according to one aspect of the present invention.

FIG. 5 shows a thermal mass type flowmeter according to one aspect of the present invention.

DETAILED DESCRIPTION OF THE PREFERRED EMBODIMENT

Preferred embodiments of the present invention are disclosed with reference to the drawings. However, it is to be understood that these preferred embodiments merely exemplify the invention which may take forms different from the specific embodiments disclosed. The drawings and dimensions provided are for the purpose of illustration. The invention is not limited to these specifics.

Figure 1:
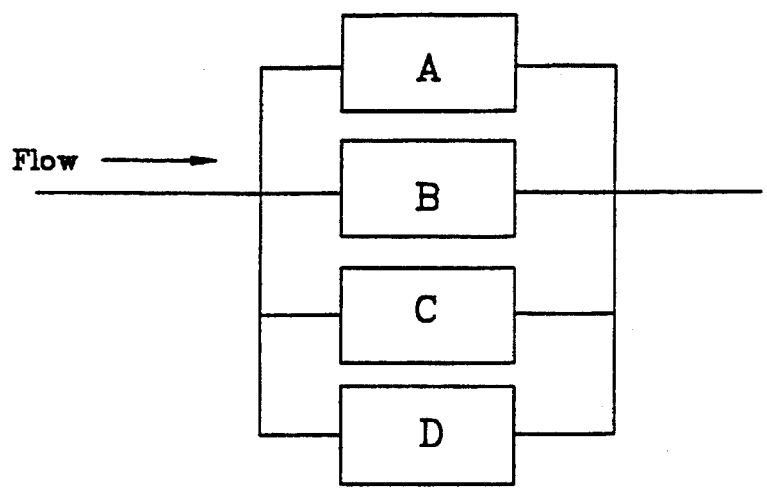
FIG. 1 is a schematic representation of multiple fluid flow paths.

FIG. 1 is a schematic representation of fluid flow paths through a flowmeter. PATH A represents a passage (or flow path), for example, the passage through which the measurement is performed, and PATHS B, C, etc., represent the main passage or passages. Multiple measurement passages may be provided. One or more of the fluid flow paths may be through a rectangular channel laminar flow element. According to one preferred embodiment of the present invention, adjustability of the full scale flow rate of a rectangular channel laminar flow element is provided.

Figure 2:
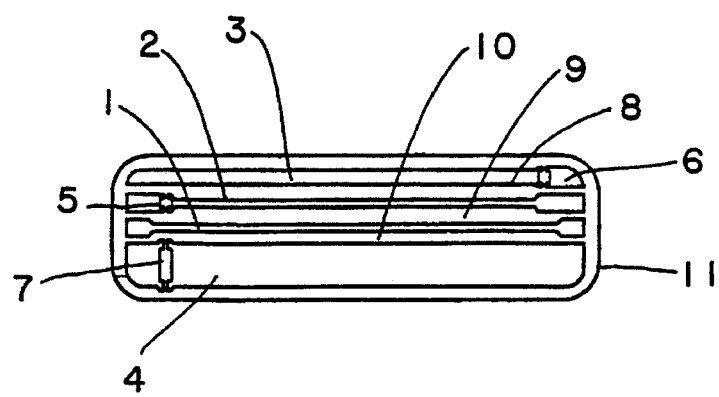
FIG. 2 shows the top view of a laminar flow element according to one aspect of the present invention.

FIG. 2 shows a preferred embodiment of the present invention. According to this preferred embodiment one or more rectangular plates 11 are provided. Plates 11 comprise rectangular channel laminar flow elements which define a laminar flow channel or laminar flow channels. Laminar flow is assured by making the characteristic dimension D (used to calculate Reynolds number) small compared to the length L of the channel. As shown in FIG. 2, for example, channels 1, 2, 3 and 4 are formed in a stainless steel plate 11. Preferably, the channels 1–4 are chemically etched in stainless steel plate 11. The thickness of the plate 11 (i.e., the dimension perpendicular to the plane of the drawing), determines the depth of the channels since these channels are etched all the way through the plate 11. Tabs 5, 6 and 7 are provided in channels 2, 3 and 4, respectively. Tabs 5–7 block fluid flow through channels 2–4, respectively. Tabs 5–7 preferably are removably attached to plate 11 and are positioned so that unless removed, fluid cannot flow through the respective channel. Preferably, channel 1 is not blocked so fluid may always pass therethrough. This channel has predetermined characteristics corresponding to a particular full scale flow rate. By selectively removing one or more tabs 5–7, the effective characteristics are changed yielding a different full scale flow rate. For example, removal of tab 5 permits fluid to flow through Channels 1 and 2. Likewise, removal of tabs 6 or 7 will permit the passage of fluid through channels 1 and 3 or 1 and 4, respectively. Walls 8, 9 and 10 can also be removed if desired.

Figure 3:
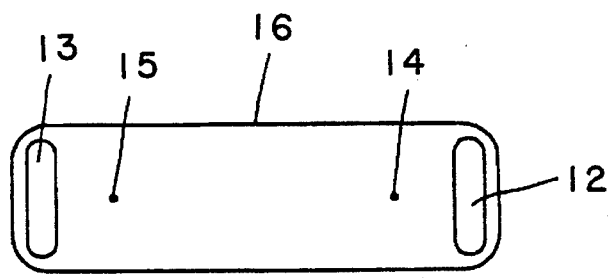
FIG. 3 shows an example of an end plate according to one aspect of the present invention.

FIG. 3 shows an end plate 16 which is uniquely designed to cooperate with the novel laminar flow element of FIG. 2. End plate 16 is provided with two holes 14 and 15 for pressure measurement. The outside dimensions of plate 16 are the same as those of plate 11. It may also be of the same thickness, but this is not necessary. Openings 12 and 13 are provided adjacent to the ends of end plate 16 and preferably are substantially aligned with the ends of the channels 1–4.

Openings 12 and 13 serve as the entry and exit ports for the channels 1–4. Holes 14 and 15 are positioned to be aligned with channel 1 to permit measurement of the flow through Channel 1. These holes are preferably placed a sufficient distance from the entry and exit port to ensure that the measurement point is at a point where laminar flow will occur (e.g., 8 diameters away from the ports).

Figure 6:
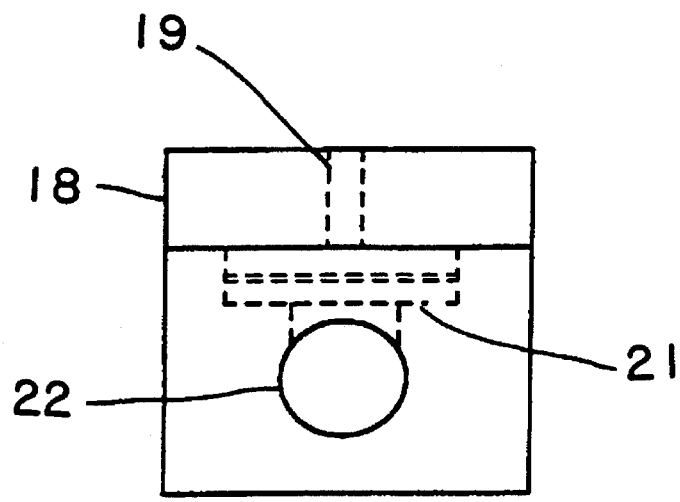
FIG. 6 is a partial end view of a laminar flowmeter according to one embodiment.
Figure 7:
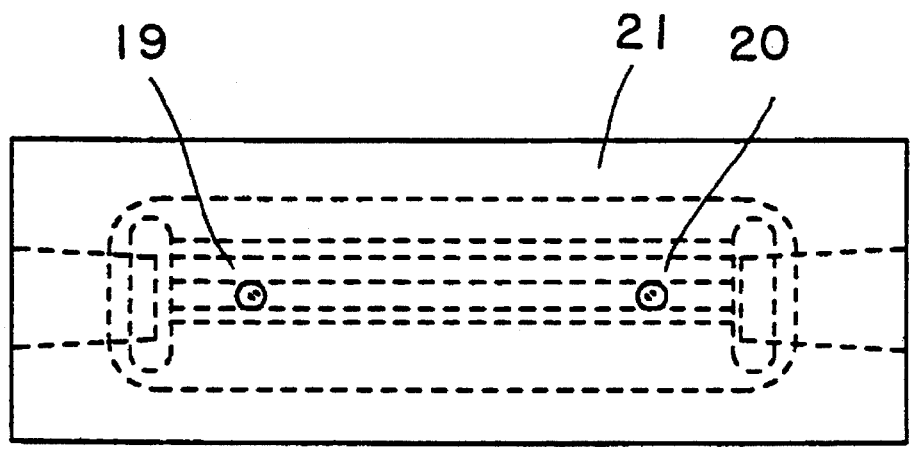
FIG. 7 is a top view of a laminar flowmeter according to one embodiment.

FIG. 4 shows the laminar flow element 11 and end plate(s) 16 arranged in a laminar flow meter housing that allows for connection of fittings and tubing on two sides and for connection of a measuring instrument such as a differential pressure transducer through the top. Other configurations may also be used. In this embodiment, fluid enters through the fitting 22 and passes through the laminar flow element 11, which is sandwiched between a top and a bottom end plate 16, and exits fitting 23. Plate 18 forms the top portion of the housing and is placed over the laminar flow element 11 and plate(s) 16 with proper gaskets after the laminar flow element(s) 11 and plate(s) 16 are placed inside groove 21 which is cutout to a size to permit it to receive the element 11 and plate 16, as best seen in FIGS. 6 and 7. Holes 19 and 20 are formed in the housing to permit pressure measurement through holes 14 and 15. A differential pressure transducer 24 may be used to measure static pressure difference across the laminar flow element that is created by the passage of fluid therethrough. Based on the linearity of flow rate and pressure for a laminar flow, the pressure may be used, in a known manner to determined the flow rate. Details of a laminar flow meter and its operation are generally known.

FIG. 5 shows on alternative arrangement to that of FIG. 4. wherein the primary difference is that a thermal mass flow measurement device is used instead of the differential pressure transducer. Preferably, stainless steel tubing 25 is placed in holes 19 and 20 which in turn connect to holes 14 and 15. Tubing 25 is used to provide a passage for a small portion of the fluid. Resistance temperature detectors, 26 and 27, are wrapped around the stainless steel tubing, 25, to provide the thermal mass flow measurement mechanism in a manner known to those skilled in the art.

TABLE I

| Flow Rate | Depth (D) of Channel (inches) | Width (W) of Channel (inches) | Reynolds Number | Pressure Drop (inches of water column) | Remove Tabs or Walls |
|---|---|---|---|---|---|
| Using 1 Laminar Flow Element | | | | | |
| 25 cc/min | .004 | .025 | 85 | 15.3 | None |
| 50 cc/min | .004 | .050 | 92 | 13.3 | 5 |
| 100 cc/min | .004 | .100 | 95 | 12.3 | 5, 6 |
| 200 cc/min | .004 | .193 | 100 | 12.3 | 5, 7 |
| Using 2 Laminar Flow Elements (with no solid plates therebetween) | | | | | |
| 500 cc/min | .008 | .075 | 596 | 11.6 | 6 |
| 1000 cc/min | .008 | .140 | 669 | 11.4 | 5, 6, 8 |
| 2000 cc/min | .008 | .250 | 767 | 12.1 | 5, 6, 7 |
| 2500 cc/min | .008 | .300 | 803 | 12.5 | 5, 6, 7, 9, 10 |
| Using 4 Laminar Flow Elements (2 Pairs of Adjacent Laminar Flow Elements with a Plate 16 Between Pairs) | | | | | |
| 5000 cc/min | .008 | .600 | 814 | 12.2 | 5, 6, 7, 9, 10 |

The values in this table provide an example of the operability of one embodiment of the present invention. These values relate to a differential pressure type flowmeter that is used to measure the flow rate of air, in connection with the laminar flow element 11 of FIG. 2.

I claim:

1. A laminar flow element for use in a laminar flow meter, said laminar flow element comprising:

first and second end plates;

a first substantially rectangular plate, located between said first and second end plates, defining a first unobstructed substantially rectangular fluid flow channel defined by a first aperture extending through said rectangular plate, said rectangular plate comprising a plurality of additional substantially rectangular fluid flow channels formed therein by a plurality of additional apertures extending through said rectangular plate, each of said additional channels being substantially parallel to said first channel and having a removably attached blocking means associated therewith to block a flow of fluid through a cross section of said respective additional channel s unless said blocking means is removed, whereby said blocking means may be removed from one or more of said additional channels, so that various fluid flow rates may be passed through a cross section of said first channel and cross sections of said one or more of said plurality of additional channels while ensuring laminar flow conditions along at least a portion of said first channel and said one or more of said plurality of additional channels.

2. The laminar flow element of claim 1 wherein at least one of said first and second end plates comprises a second substantially rectangular plate having dimensions substantially identical to dimensions of said first substantially rectangular plate and having at least two holes formed therein for permitting measurement of characteristics of fluid passing through at least said first channel, wherein said two holes are formed in a location of said second substantially rectangular plate which corresponds to the location of at least a portion of said first channel in said first substantially rectangular plate, said at least one end plate cooperating with said first substantially rectangular plate to block a flow of fluid through said respective additional channel unless said blocking means is removed 3. A laminar flow meter comprising:

a housing;

a support located within said housing for supporting at least one laminar flow element and at least one end plate;

said laminar flow element comprising a first substantially rectangular plate comprising a first unobstructed substantially rectangular fluid flow channel formed therein and defined by a first aperture extending through said first plate, a plurality of additional substantially rectangular fluid flow channels formed therein and defined by a plurality of additional apertures extending through said first plate, each of said additional channels being substantially parallel to said first channel and having a removably attached blocking means associated therewith to block a flow of fluid through a cross section of said respective additional channel unless said blocking means is removed, whereby said blocking means may be removed from one or more of said additional channels, so that various fluid flow rates may be passed through a cross section of said first channel and cross sections of one or more of said plurality of additional channels while ensuring laminar flow conditions along at least a portion of said first channel and said one or more additional channels;

said at least one end plate comprising a second substantially rectangular plate having dimensions substantially identical to dimensions of said first substantially rectangular plate and having at least two holes formed therein for permitting measurement of characteristics of fluid passing through at least said first channel, wherein said two holes are formed in a location of said second substantially rectangular plate which corresponds to the location of at least a portion of said first channel in said first substantially rectangular plate, said at least one end plate cooperating with said first substantially rectangular plate to block a flow of fluid through said respective additional channel unless said blocking means is removed; and a measurement means operatively connected to said two holes for measuring a characteristic of said fluid passing through said first channel.

4. The laminar flowmeter of claim 3 wherein said measurement means comprises a differential pressure sensor.

5. The laminar flowmeter of claim 3 wherein said measurement means comprises a thermal mass detector.

6. A laminar flow element for use in a laminar flow meter, said laminar flow element comprising:

a plurality of substantially rectangular plates, each plate having a first aperture formed therethrough and a plurality of additional apertures formed therethrough, the apertures of each of said plates being substantially identical in shape to corresponding apertures of the remaining of said plates, said plurality of plates being positioned adjacent one another so that the apertures of each of said plates are substantially aligned with corresponding apertures of the remaining of said plates, and such that said plates so positioned have a first end and a second end;

a first end plate positioned adjacent said first end; and a second end plate positioned adjacent said second end, wherein each said first aperture, together with said first and second end plates, defines a first unobstructed substantially rectangular fluid flow channel, and wherein each said plurality of additional apertures, together with said first and second end plates, define a plurality of additional substantially rectangular fluid flow channels, which are substantially parallel to said first channel, said additional channels each having a removably attached blocking means associated therewith to block a flow of fluid through said respective additional channel unless said blocking means is removed, and wherein said blocking means may be removed from one or more of said additional channels to permit various fluid flow rates through said first channel and said one or more of said additional channels while ensuring laminar flow conditions along at least a portion of said first channel and said one or more of said additional channels.

7. The laminar flow element of claim 6 wherein at least one of said first and second end plates has at least two holes formed therein at a location of said at least one end plate, which corresponds to the location of at least a portion of said first channel, such that said two holes permit measurement of characteristics of fluid passing through at least said first channel.

8. The laminar flow element of claim 6 wherein each of said blocking means comprises a plurality of blocking tabs, at least one of said blocking tabs being disposed in each of the corresponding ones of said plurality of additional apertures, said blocking tabs being substantially aligned to block a flow of fluid through said respective additional channel unless at least one of said blocking tabs is removed.

* * * * *